US008303534B2

(12) United States Patent
Hickle et al.

(10) Patent No.: US 8,303,534 B2
(45) Date of Patent: *Nov. 6, 2012

(54) REMOTE MONITORING AND CONTROL OF SEDATION AND ANALGESIA SYSTEMS

(76) Inventors: Randall S. Hickle, Lubbock, TX (US); Nicholas E. Cobb, Lubbock, TX (US); William Patrick Adair, Lubbock, TX (US)

( * ) Notice: Subject to any disclaimer, the term of this patent is extended or adjusted under 35 U.S.C. 154(b) by 1111 days.

This patent is subject to a terminal disclaimer.

(21) Appl. No.: 10/372,666

(22) Filed: Feb. 25, 2003

(65) Prior Publication Data
US 2003/0176774 A1    Sep. 18, 2003

Related U.S. Application Data

(60) Provisional application No. 60/358,729, filed on Feb. 25, 2002.

(51) Int. Cl.
*A61M 31/00* (2006.01)
(52) U.S. Cl. ............ 604/66; 604/93.01; 604/500; 705/2
(58) Field of Classification Search .............. 604/65–67, 604/93.01, 500; 600/301, 300; 705/2
See application file for complete search history.

(56) References Cited

U.S. PATENT DOCUMENTS

| | | | |
|---|---|---|---|
| 4,551,133 A * | 11/1985 | Zegers de Beyl et al. ...... | 604/66 |
| 4,685,903 A * | 8/1987 | Cable et al. ................... | 604/154 |
| 4,731,051 A | 3/1988 | Fischell | |
| 4,898,579 A * | 2/1990 | Groshong et al. ............. | 604/67 |
| 5,020,528 A | 6/1991 | Myers ...................... | 128/202.13 |
| 5,036,852 A | 8/1991 | Leishman ..................... | 128/630 |
| 5,357,427 A | 10/1994 | Langen et al. ........... | 364/413.02 |
| 5,544,649 A | 8/1996 | David et al. .................... | 128/630 |
| 5,553,609 A | 9/1996 | Chen et al. .................... | 128/630 |
| 5,558,638 A | 9/1996 | Evers et al. ..................... | 604/66 |
| 5,594,786 A | 1/1997 | Chaco et al. .................... | 379/93 |
| 5,626,144 A | 5/1997 | Tacklind et al. .............. | 128/725 |
| 5,687,717 A | 11/1997 | Halpern et al. ................ | 128/630 |
| 5,704,366 A | 1/1998 | Tacklind et al. .............. | 128/716 |
| 5,732,709 A | 3/1998 | Tacklind et al. .............. | 128/726 |
| 5,738,102 A | 4/1998 | Lemelson ..................... | 128/671 |
| 5,752,917 A | 5/1998 | Fuchs ........................... | 600/484 |
| 5,788,688 A | 8/1998 | Bauer et al. | |
| 5,829,444 A | 11/1998 | Ferre et al. .................... | 128/897 |
| 5,855,550 A | 1/1999 | Lai et al. ....................... | 600/300 |

(Continued)

FOREIGN PATENT DOCUMENTS

DE    100 05 526 A1    8/2001

(Continued)

*Primary Examiner* — Theodore Stigell
(74) *Attorney, Agent, or Firm* — Dorsey L Baker

(57) ABSTRACT

The present invention comprises a sedation and analgesia system having integrated patient monitoring and drug delivery, where information related to monitored patient parameters and drug delivery is accessible and controllable from a remote location. Information relative to monitored patient parameters and drug delivery may be provided in real-time or near real-time, to an attending nurse, physician, insurance company, billing department, or other suitable party according to the present invention via a computing device, video monitor, over the Internet, over an intranet, or by any other suitable means of transmitting and displaying critical data. The present invention further comprises an integrated in-room monitor, where data related to critical patient parameters and drug delivery may be integrated with other means of communicating data related to a patient, a procedure, or a medical device.

21 Claims, 4 Drawing Sheets

U.S. PATENT DOCUMENTS

| | | | | |
|---|---|---|---|---|
| 5,931,791 | A | 8/1999 | Saltzstein et al. | 600/513 |
| 5,941,829 | A | 8/1999 | Saltzstein et al. | 600/509 |
| 5,944,659 | A | 8/1999 | Flach et al. | 600/300 |
| 5,957,885 | A * | 9/1999 | Bollish et al. | 604/67 |
| 6,006,191 | A | 12/1999 | DiRienzo | 705/2 |
| 6,151,581 | A * | 11/2000 | Kraftson et al. | 705/3 |
| 6,186,977 | B1 | 2/2001 | Andrews et al. | |
| 6,302,844 | B1 * | 10/2001 | Walker et al. | 600/300 |
| 6,358,203 | B2 | 3/2002 | Bardy | 600/300 |
| 6,470,234 | B1 * | 10/2002 | McGrady | 700/241 |
| 6,564,104 | B2 | 5/2003 | Nelson et al. | 607/60 |
| 6,579,242 | B2 | 6/2003 | Bui et al. | |
| 6,807,965 | B1 * | 10/2004 | Hickle | 128/204.23 |
| 6,928,490 | B1 * | 8/2005 | Bucholz et al. | 709/249 |
| 2001/0023315 | A1 | 9/2001 | Flach et al. | 600/300 |
| 2001/0037366 | A1 | 11/2001 | Webb et al. | 709/204 |
| 2001/0044823 | A1 * | 11/2001 | Labounty et al. | 709/203 |
| 2002/0017299 | A1 * | 2/2002 | Hickle | 128/204.21 |

FOREIGN PATENT DOCUMENTS

| | | |
|---|---|---|
| EP | 1 034 734 A1 | 9/2000 |
| WO | WO 98/38909 | 9/1998 |
| WO | WO 99/59460 | 11/1999 |
| WO | WO 99/62403 | 12/1999 |
| WO | WO 9962403 A1 * | 12/1999 |
| WO | WO 01/24690 A2 | 4/2001 |

* cited by examiner

REMOTE MONITORING AND CONTROL OF SEDATION AND ANALGESIA SYSTEMS

CROSS-REFERENCE TO RELATED APPLICATIONS

This application claims priority under 35 U.S.C. §119(e) from U.S. Provisional Patent Application Serial No. 60/358,729, filed Feb. 25, 2002 and incorporated herein by reference.

FIELD OF THE INVENTION

The present invention relates, in general, to sedation and analgesia systems and, more particularly, to sedation and analgesia systems having remote data storage, monitoring and control functionalities.

BACKGROUND OF THE INVENTION

Medical telemetry systems that allow physiologic data from multiple, remotely-located patients to be monitored from a central location are known in the art. These systems typically comprise remote telemeters that remotely collect the physiologic data of respective patients and transmit the data over a wireless or land-based link to a monitoring station. This physiologic data may include, for example, real-time electrocardiograms (EKG), carbon dioxide levels, blood pressure, temperature, respiration rates, and other critical patient parameters. From the monitoring station, a clinician can, in real-time, monitor the physiologic status of many different patients. The central station may also run automated monitoring software for alerting the clinician whenever a predetermined physiologic event occurs, such as a cardiac arrhythmia condition.

The remote telemeters of medical telemetry systems are generally of two types: instrument remote telemeters and ambulatory remote telemeters. An ambulatory remote telemeter is a portable, battery-powered device which permits the patient to be monitored while the patient is ambulatory. The ambulatory telemeter attaches to the patient by a strap or other attachment device, and receives the patient's physiologic data via EKG leads and/or other types of sensor leads, which attach to the patient's body. The physiologic data is continuously transmitted to the central monitoring station by the telemeter's radio frequency (RF) transmitter to permit real-time monitoring. Instrument remote telemeters operate in a similar manner, but receive the patient's physiologic data from a bedside monitor, or other instrument, over a hardwired line, such as an RS-232 connection. Instrument remote telemeters that transfer the physiologic data to the monitoring station over a hardwired connection are also found.

Typically, the monitoring station includes a receiver for receiving and decoding RF transmissions from the patient transmitter, and a computer for displaying the physiologic data. In many cases, the receivers are implemented as circuit boards that plug into a standard personal computer. The resulting physiologic data is displayed on the computer screen. In these applications, the process of collecting data and updating the display is relatively simple because the receiver, computer, and display are combined in a single system.

Computer networks capable of facilitating the display of physiologic telemetry data are also found in the art. In such systems, the data is often transmitted over a dedicated network, using hardware and software, to various work-station computers interspersed throughout a hospital. Existing network systems also employ hardware and software designed for a packet switched network. In such systems, monitored physiologic data is transmitted to a central data-monitoring device, where one or more waveform servers are connected to the central data-monitoring device and to a computer network. One or more data servers are also connected to the computer network. In these systems, the waveform servers receive the physiologic information from the central data-monitoring device and supply the physiologic data to one or more workstations.

Presently, many medical applications benefit from the use of visual display systems such as, for example, video monitors, where information viewed by a clinician through an endoscope, colonoscope, or other medical instrument is displayed on a video monitor located in the room. Generally, video monitors and other visual display systems used in this capacity provide video images in real-time taken by a camera integrated with an intracorporeal medical device. Though such systems are helpful in diagnosing a patient's condition or performing a procedure, clinicians generally require separate monitors for monitored patient parameters and video images recorded by medical scopes. The use of multiple monitors in chaotic environments such as, for example, hospital operating rooms, may lead to hazardous situations as a result of superfluous AC power cords or bulky obtrusive equipment. Further, clinicians relying on multiple monitors often have difficulty dedicating their full attention to a patient's overall condition, where the use of a plurality of monitors requires the clinician to constantly switch back and forth between monitors. Furthermore, the configuration of different display devices relative to each other at a given location may vary from one operating/procedure room to the other, requiring clinicians to re-orient themselves with each new room and creating a risk of reading displayed data from the wrong display device. Where multiple monitors are used in medical applications, there is the potential for clinicians to miss critical patient episodes while viewing a monitor not displaying information related to the negative episode. The need has therefore arisen for an in-room remote monitoring system that displays information from a sedation and analgesia system related to critical patient parameters and drug delivery in cooperation with images received from medical scopes. The need has further arisen for an integrated monitor that may combine and display data from a sedation and analgesia system with any other suitable display such as, for example, patient histories or an expert's commentary.

Though certain existing monitoring systems feature some remote functionality, the need remains for sedation and analgesia systems with a remote functionality. The need has arisen for an integrated sedation and analgesia system that remotely transmits and/or displays information related to both a patient's physiologic condition and actions taken by the sedation and analgesia system in response to that patient's physiologic condition. The need has further arisen for a means of providing data in a real-time fashion, enabling remote systems to be utilized in a supervisory capacity, a teaching capacity, to provide compliance with the Joint Commission on Accreditation of Healthcare Organizations (JCAHO) requirements and other regulatory agencies, and/or for use in transmitting information related to drug use and patient billing, among others.

SUMMARY OF THE INVENTION

The present invention comprises a sedation and analgesia system having integrated patient monitoring and drug delivery, where information related to monitored patient parameters and drug delivery is accessible from a remote location.

The invention provides data, accessible from a remote location in real-time or near real-time, to an attending nurse, physician, insurance company, billing department, or other suitable party. Remote interfaces herein include those not physically mounted to a corresponding fixed unit, such as a sedation and analgesia system. A remote device or interface could be a few feet from the fixed unit or thousands of mile away. The connection between the remote device or interface and the fixed unit may be wired or wireless. Information relative to monitored patient parameters and drug delivery may be provided according to the present invention via a personal computer or computing device, video monitor, over the Internet, over an intranet, or by any other suitable means of relaying and displaying critical data. This data may, for example, be used in a quality audit in order to comply with regulatory standards.

The present invention further comprises an integrated in-room monitor, where data related to critical patient parameters and drug delivery may be integrated with other means of communicating data related to a patient, a procedure, or a medical device. The invention also may include a means of storing data related to critical patient parameters in a remote location. The remote means allows the controlling of one or a plurality of sedation and analgesia systems, where proper drug use, proper drug dosage delivery, system misuse, and system maintenance could be monitored.

DETAILED DESCRIPTION OF THE INVENTION

Figure 1:
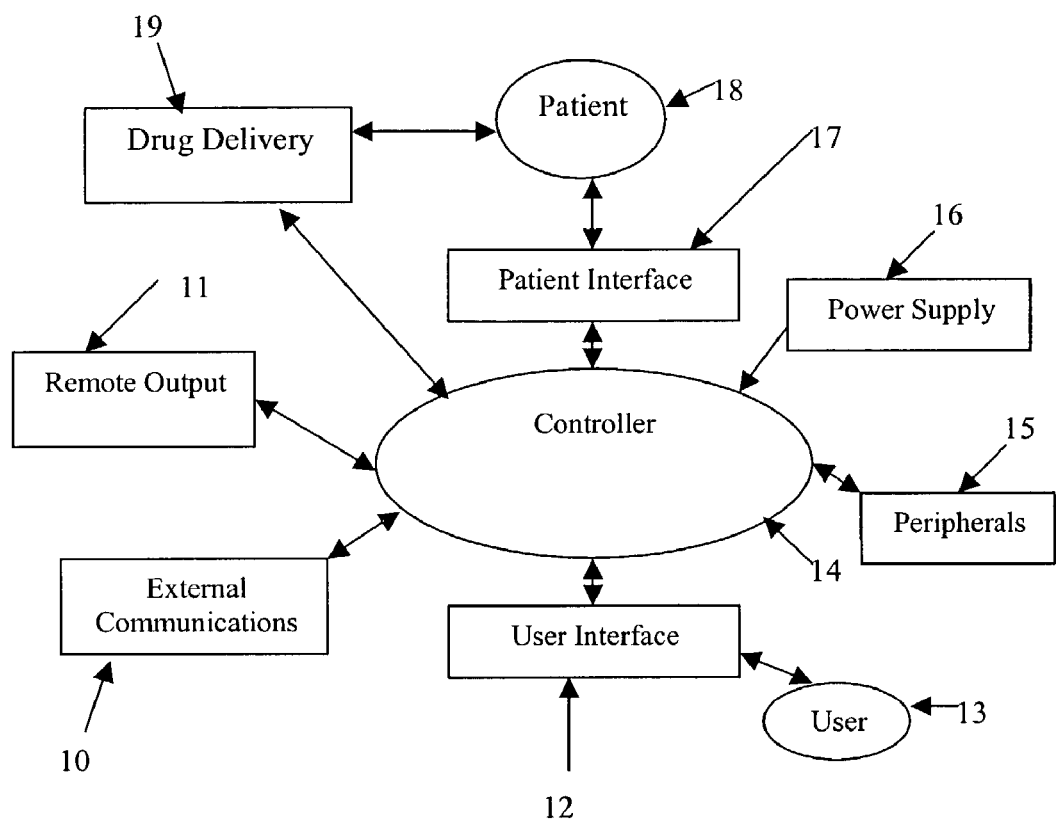
FIG. 1 illustrates a block diagram of one embodiment of a sedation and analgesia system in accordance with the present invention.

FIG. 1 illustrates a block diagram depicting one embodiment of the present invention comprising sedation and analgesia system 22 having user interface 12, software controlled controller 14, peripherals 15, power supply 16, external communications 10, remote output 11, patient interface or physical monitor 17, and drug delivery 19, where sedation and analgesia system 22 is operated by user 13 in order to provide sedation and/or analgesia to patient 18. An example of sedation and analgesia system 22 is described in commonly assigned and co-pending U.S. patent application Ser. No. 09/324,759, filed Jun. 3, 1999 and incorporated herein by reference.

The sedation and analgesia system of application Ser. No. 09/324,759 includes a patient health monitor device adapted so as to be coupled to a patient and generate a signal reflecting at least one physiological condition of the patient, a drug delivery controller supplying one or more drugs to the patient, a memory device storing a safety data set reflecting safe and undesirable parameters of at least one monitored patient physiological condition, and an electronic controller interconnected between the patient health monitor, the drug delivery controller, and the memory device storing the safety data set; wherein said electronic controller receives said signals and in response manages the application of the drugs in accord with the safety data set.

Figure 2:
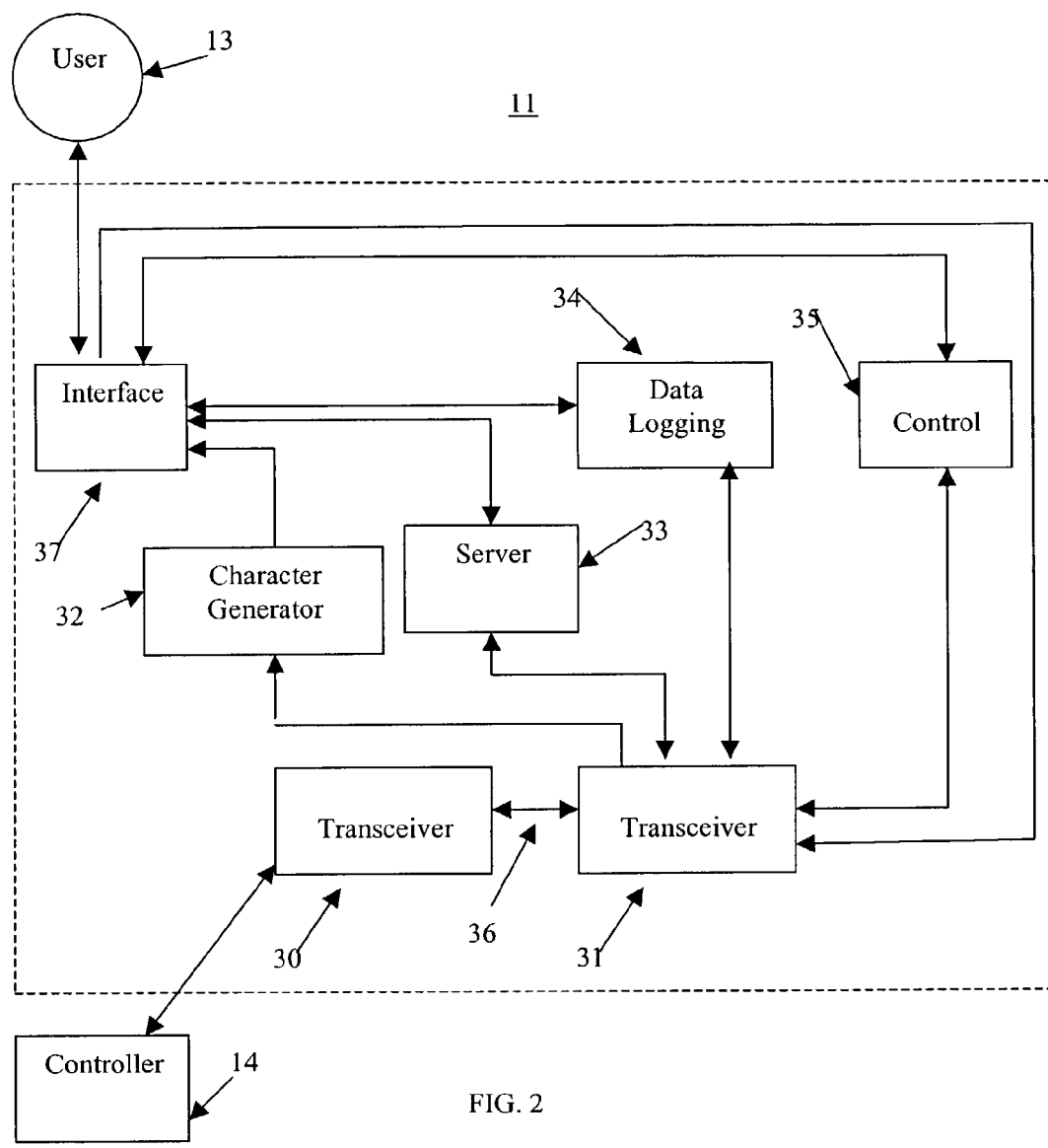
FIG. 2 illustrates a block diagram of one embodiment of a remote output system in accordance with the present invention.

FIG. 2 illustrates a block diagram depicting a more detailed view of remote output 11 in cooperation with controller 14. In one embodiment of the present invention remote output 11 comprises first transceiver 30, second transceiver 31, character generator 32, server 33, data logging 34, control 35, connection 36, and interface 37, where user 13 interacts with interface 37. First transceiver 30 may be a transmitter and receiver in parallel, a transmitter, or any other suitable transmission device. Second transceiver 31 may be a transmitter and receiver in parallel, a receiver, or any other suitable transmission device. Data received by controller 14 regarding patient 18 monitoring, drug delivery, or other critical parameters may be transmitted from first transceiver 30 to second transceiver 31 via connection 36. Connection 36 may be a wireless connection or a hardwired connection. In the wireless embodiment of the present invention, connection 36 may be wireless Ethernet, Blue Tooth, infrared or any other suitable wireless connection. In the hardwired embodiment of the present invention, connection 36 may transmit an analog signal via a fixed VGA port, a digital signal via an RS-232 connection, a parallel port, wired Ethernet, or by any other suitable transmission means. The present invention further comprises electrically isolating first transceiver 30 and/or second transceiver 31. Connections between other elements of sedation and analgesia system 22 may be by way of serial ports, parallel ports, or by any other suitable transmission means.

Interface 37 may comprise personal computers or computing devices, a plurality of monitors or terminals interconnected through a network, one or a plurality of isolated VGA monitors, video monitors, and/or any other suitable visual display. Interface 37 may also comprise auditory or tactile communication means. Interface 37 further comprises a means of inputting user 13 modifications into remote output 11, where the input means may be at least one selected from the group consisting of a keyboard, a pointing device such as a mouse or trackball, a touchpad, a joystick, a voice responsive system, or any other suitable input means.

In one embodiment of the present invention second transceiver 31 may be adapted to transmit data to character generator 32, where selective data may be transmitted to and displayed on interface 37. Character generator 32 may be a digital video character generator having digital video, S-video, and composite video inputs and outputs. Character generator 32 may also be a reconfigurable character generator (RCG), such as those made by Delphi, where the RCG may be a custom integrated circuit capable of driving an LCD display at $\frac{1}{14}$ duty, $\frac{1}{5}$ bias, to a maximum of 10 volts. The integrated circuit may contain 96 late-programmable ROM and 32 RAM alpha-graphic characters which may be selected for message display. Any suitable character generator may be integrated with sedation and analgesia system 22. Providing character generator 32 integrated with interface 37 and controller 14 allows data to be displayed on an existing video display used in medical procedures such as, for example, displays used in endoscopies. Further, providing character generator 32 allows only specific data relevant to a particular application to be displayed simultaneously with video transmissions. For example, a physician performing an endoscopy may determine that one or more of drug delivery levels from sedation and analgesia system 22, patient 18 heart rate, and patient 18 blood pressure are especially critical parameters. The present invention comprises displaying data relative to such critical parameters simultaneously as an overlay or as a picture-in-picture display or as a multi-layer display (such as Deep Video) on in-room monitors while displaying endoscopic video transmissions. Displaying patient and drug delivery data in such a way may diminish the number of monitors present in often cluttered operating rooms and ambulatory medical centers. Integrating patient and drug delivery data with procedural video transmissions into a single display also focuses the attention of the attending physician, reducing the probability of missed negative patient episodes. A single monitor also facilitates implementing conventions whereby certain data are always displayed at certain locations at certain times where these conventions are aimed at helping clinicians working at different locations to quickly orient themselves.

In one embodiment of the present invention, second transceiver 31 is adapted to transmit data to server 33, where server 33 may link to an intranet, an extranet, and/or the Internet. In one embodiment of the present invention, interface 37 may be any PC or computing device linked into a network connected to server 33, where user 13 is any authorized individual monitoring patient parameters and drug delivery associated with sedation and analgesia system 22 over the network. It is contemplated that if an expert in a particular medical field is unable to monitor or assist in a medical procedure in person, they may do so over a network, where data related to patient monitoring and sedation and analgesia system 22 will be available in real-time or near real-time. The present invention further comprises allowing an authorized remote user 13 to modify sedation and analgesia system 22 in the event a malfunction or negative patient episode has occurred. The present invention further comprises providing an internal intranet where, for example, only consoles or computing devices associated with a hospital have access to remote sedation and analgesia system 22 data. One embodiment of the present invention comprises allowing only authorized individuals to actively participate remotely in a medical application, while allowing other consoles to be used in a strictly teaching capacity as observers. The present invention comprises incorporating security measures such as, for example, user personal identification numbers that must be inputted before the user may access a remote terminal, voice recognition systems and other bio-metric means of authentication, virus protection, and protection against hackers. Providing remote access via extranets and/or intranets may benefit students by providing a teaching means, patients by permitting experts to assist in medical procedures from remote locations, hospitals by allowing data from sedation and analgesia system 22 to be collected for billing purposes, and regulatory agencies such as for example, JCAHO, by providing data related to regulatory healthcare compliance.

The present invention further comprises second transceiver 31 adapted to transmit data to data logging 34, where data logging 34 comprises a hard drive, a flash disk, a super disk, USB drive or any other suitable storage means. The present invention further comprises storing data related to sedation and analgesia system 22 in a flash disk, super disk, USB drive or other storage means housed in sedation and analgesia system 22. For example, data related to drug delivery and patient monitoring may be recorded in a flash disk incorporated into sedation and analgesia system 22, where the data storage device may be manually removed and transported to an appropriate interface 37. Providing a flash disk or super disk allows for stored data to be readily transferred from data logging 34, where information relative to a medical procedure may be, for example, transferred with a patient to any necessary location. Data logging 34 comprises the storage of data associated with any parameter related to sedation and analgesia system 22 and/or patient 18. Data associated with data logging 34 may be viewed and/or modified through interface 37, where interface 37 may be a PC, computing device or any other suitable interface. Data routed through data logging 34 may be determined by controller 14, where parameters desirable for storage may be pre-programmed or initiated by user 13. Data logging 34 further functions to store data necessary for compliance with JCAHO and other regulatory agencies.

In one embodiment of the present invention, data logging 34 comprises a data acquisition system (not shown), where the data acquisition system receives data from sedation and analgesia system 22 regarding monitored patient 18 parameters, user 13 input, drug delivery events, sedation and analgesia system 22 software functionality, sedation and analgesia system 22 hardware functionality, and/or other system and/or patient parameters at predetermined intervals. Providing data logging 34 with the functionality to monitor such parameters as, for example, software functionality and drug delivery levels, at predetermined intervals allows for sedation and analgesia system 22 to be evaluated for malfunction in the event of a negative patient episode, where the negative episode may be the result of a sedation and analgesia system 22 malfunction. Data obtained by the data acquisition system may be stored internally in sedation and analgesia system 22 by a flash disk, super disk, hard drive, USB drive or other suitable storage device, or may be transmitted externally to server 33 and/or control 35. Data acquisition regarding sedation and analgesia system 22 functionality and patient 18 condition may be taken at any suitable predetermined time period, where enough data is gathered to sufficiently evaluate the cause of a system problem. For example, a patient's temperature may vary, under normal circumstances, at a rate of about 1 degree an hour, whereas a patient's heart rate may change substantially in a much shorter period. The present invention comprises providing data logging 34 with the capability to record data from different patient 18 and/or sedation and analgesia system 22 parameters at different time intervals, where the time interval will depend on the amount of data required to evaluate the system and/or the condition of patient 18 at the time of a suspected malfunction. For example, data related to patient 18 body temperature may be recorded in data logging 34 every ten minutes, whereas data related to patient 18 heart rate may be recorded every 5 seconds. Storing data in data logging 34 provides researchers and/or system maintenance personnel with the ability to evaluate the functionality of sedation and analgesia system 22 as sedation and analgesia system 22 interacts with patient 18, in order to ascertain whether a malfunction occurred, and if so, where the malfunction occurred and what effects the malfunction had on patient 18 and/or sedation and analgesia system 22. The present invention comprises storing data in data logging 34 for a predetermined period of time such as, for example, 180 days, where ample time is provided to researchers to evaluate a case before the data is expunged. Other suitable time frames for data storage such as, for example, days, months, or years, are consistent with the present invention.

The present invention further comprises second transceiver 31 adapted to transmit data to control 35, where control 35 may be a PC, a microcontroller, a programmable controller, or other suitable computing or data processing device, where control 35 may be integral with interface 37, integral with controller 14, or independent. Control 35 may also be software in a suitable language such as, for example, C++, associated with controller 14 or interface 37.

In one embodiment of the present invention, control 35 comprises regulating the use of proper drugs, the use of proper drug amounts, the measurement of critical performance indicators of sedation and analgesia system 22 to predict when sedation and analgesia system 22 failure is imminent, misuse of sedation and analgesia system 22, monitoring the outcome of procedures for quality assurance analysis, calculating how many hours the system has been in use, the use-state of the system, and/or billing associated with sedation and analgesia system 22. Control 35 comprises regulating the use of proper drugs by incorporating, for example, a bar code scanner with interface 37, where interface 37 may be a PC or computing device located in a pharmacist's office, a regulatory agency, or other suitable monitoring location. The present invention comprises allowing pharmacists or other authorized individuals to scan bar codes or other identification markers or tags, such as those described in U.S. patent application Ser. No. 10/252,818 filed Sep. 24, 2002, which are associated with quality-certified drugs into control 35. Data associated with certified drugs may be stored in interface 37, control 35, and/or controller 14. In one embodiment of the present invention, when a drug vial is inserted into sedation and analgesia system 22, controller 14 will transmit information relative to the drug label to control 35. If the label is consistent with a label programmed as quality-certified, sedation and analgesia system 22 may maintain normal functionality. In the event the inserted drug is not consistent with drugs programmed as quality-certified, sedation and analgesia system 22 may enter a lock-out mode. The present invention further comprises regulating the use of proper drugs by manually accepting drugs inserted into a remote sedation and analgesia system 22, reading pre-coded magnetic strips, using character recognition devices to read labels, or by any other suitable means of assuring the use of proper drugs.

Control 35 further comprises regulating proper drug dosages, where control 35 comprises programming associated with interface 37. In one embodiment of the present invention, data related to one or a plurality of sedation and analgesia systems 22 is connected to a central interface 37. Interface 37 may be a PC or other suitable computing device operated by an authorized supervisor such as, for example, an anesthesiologist or certified registered nurse anesthetist (CRNA). Control 35 comprises programming that allows for a single supervisor to monitor and control drug delivery associated with one or a plurality of medical applications employing sedation and analgesia system 22. It is further contemplated that a single supervisor may monitor one or a plurality of patients 18 from a remote location over a network such as, for example, an intranet or the Internet.

In one embodiment of the present invention, control 35 further comprises programming associated with interface 37 and/or controller 14 responsible for monitoring proper sedation and analgesia system 22 functionality. Programming associated with control 35 may take the form of binary strobes from controller 14 to interface 37, where interface 37 anticipates a strobe from controller 14 within a predetermined window. In the event interface 37 does not receive a valid strobe within a pre-determined window, programming associated with control 35 may lock-down sedation and analgesia system 22, where an invalid strobe indicates a system malfunction. It will be obvious to one of ordinary skill in the art that there are a plurality of ways of monitoring sedation and analgesia system 22 functionality from a remote location.

Control 35 further comprises ensuring proper dosage delivery by comparing the amount of drug dispensed from a drug vial to the amount dispensed indicated by sedation and analgesia system 22 such as, for example, by weighing the drug vial before and after the procedure and comparing the results to those indicated by sedation and analgesia system 22. Control 35 may also include programming associated with interface 37 and/or controller 14 related to providing an emergency "help" function. It is contemplated that sedation and analgesia system 22 may be operated manually by an authorized individual, remotely, or both. In the event that an authorized individual is monitoring sedation and analgesia system 22 in person and a supervisor is monitoring sedation and analgesia system 22 remotely, it is contemplated that the individual monitoring sedation and analgesia system 22 in person may communicate with the supervisor via control 35 and/or relinquish control to the supervisor. It is further contemplated that a communications link between a supervisor and an in-room certified attendant may occur via a network such as, for example, the Internet, an intranet or a local area network.

Figure 3:
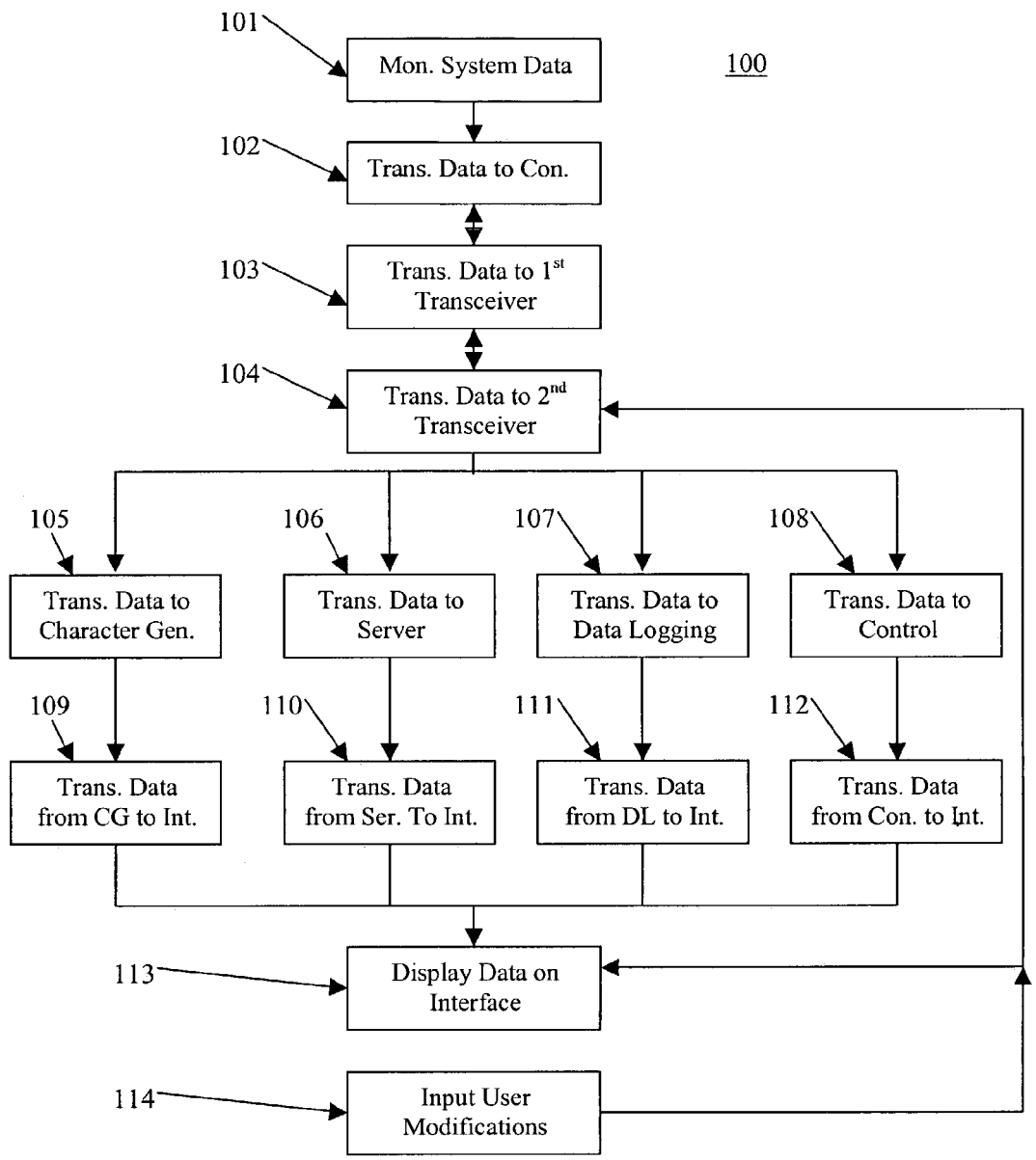
FIG. 3 illustrates a flow chart depicting one embodiment of a method for providing a remote functionality in a sedation and analgesia system in accordance with the present invention.

FIG. 3 illustrates one embodiment of a method for providing a remote functionality to a sedation and analgesia system 100, herein referred to as method 100, in accordance with the present invention. In one embodiment of the present invention, method 100 comprises monitoring system data (step 101), herein referred to as step 101. Step 101 comprises monitoring data recorded from patient peripherals such as those associated with patient interface 17 and/or drug delivery 19. Transmitting data to controller (step 102), herein referred to as step 102, comprises providing programming associated with controller 14, where programming may be related to critical thresholds, percent increases, patient response to drug delivery, or other critical parameters associated with data received from drug delivery 19 and/or patient interface 17. Programming associated with step 102 may further be designed to transmit information relative to patient condition and drug delivery to first transceiver 30.

Transmitting data to first transceiver (step 103), herein referred to as step 103, comprises controller 14 outputting to first transceiver 30 data relative to programming associated with step 102. Method 100, in one embodiment of the present invention, may then proceed to transmit data to second transceiver (step 104), herein referred to as step 104. Data may be transmitted from first transceiver 30 to second transceiver 31 via a hardwired connection, a wireless connection, or both. In the hardwired embodiment of the present invention, connection 36 connecting first transceiver 30 and second transceiver 31 may be Ethernet, a serial port such as, for example, an RS-232 connection, a parallel port, a VGA port, or any other suitable hardwired connection. Steps 103 and 104 further comprise transmitting and receiving data to and from electrically isolated first transceiver 30 and second transceiver 31. Further, first transceiver 30 associated with step 103 may be a transmitter and second transceiver 31 associated with step 103 may be a receiver where only one-way communication is permitted. In the wireless embodiment of the present invention, connection 36 connecting first transceiver 30 to second transceiver 31 may be wireless Ethernet, Blue Tooth, where Blue Tooth is a wireless personal network technology capable of transmitting 720 Kbps over 10 to 100 meters in the 2.4 GHz band, or any other suitable wireless transmission means.

Following transmission of data to second transceiver 31, method 100 may proceed to transmit data to a character generator (step 105), herein referred to as step 105, transmit data to a server (step 106), herein referred to as step 106, transmit data to data logging (step 107), herein referred to as step 107, and/or transmit data to control (step 108), herein referred to as step 108. Step 105 comprises transmitting data from second transceiver 31 associated with step 104 to character generator (CG) 32 (FIG. 2). Method 100 may then proceed to transmit data from a character generator to an interface step 109, herein referred to as step 109. Character generator 32, controller 14, and/or interface 37 may be programmed to display any desirable characters and/or waveforms on interface 37, where the display of data on interface 37 is consistent with display data on interface (step 113), herein referred to as step 113.

Step 106 comprises transmitting data from second transceiver 31 associated with step 104 to server 33. Method 100 may then proceed to transmit data from a server to an interface (step 110), herein referred to as step 110. Server 33 may transmit data to interface 37 by incorporating the use of a network such as, for example, the Internet, where interface 37 may be any authorized terminal with access to the network.

Step 107 comprises transmitting data from second receiver 31 associated with step 104 to data logging 34. Method 100 may then proceed to transmit data from data logging (DL) to an interface (step 111), herein referred to as step 111. Predetermined data parameters may be transmitted to interface 37, where data parameters are predetermined by incorporating programming into interface 37, controller 14, and/or data logging 34 associated with displaying storage information relative to critical patient parameters. Interface 37 may be any suitable display device such as, for example, a video monitor or VGA device, or any other suitable means of communicating data such as, for example, an audio or tactile output.

Step 108 comprises transmitting data from second receiver 31 associated with step 104 to control 35. Method 100 may then proceed to transmit data from control (Con.) to an interface (step 112). Control 35 may be a microprocessor, a computer programmable logic device (CPLD), a hard drive, programming associated with components of sedation and analgesia system 22, or any other suitable control means. Control 35 may be programmed to transmit suitable information to interface 37 relative to proper drug usage, proper drug dosage delivery, misuse of sedation and analgesia system 22, calls for help from user 13, patient 18 condition, healthcare compliance factors, or other suitable control parameters. Interface 37 may be a bar code reader, a VGA device, a video monitor, a storage database with visual capabilities, an audio interface, or other suitable interface.

Method 100 comprises proceeding to display data on interface (step 113), herein referred to as step 113, following steps 109, 110, 111, and/or 112. Step 113 comprises providing interface 37, where interface 37 may be a video monitor, a VGA device, a multilayer display, a heads-up display, a storage database with visual capabilities, a liquid crystal display screen (LCD) or any other suitable interface. Data may be displayed on interface 37 as an overlay, optical characters superimposed over a video transmission, a projected image onto a wall or other structure, a website, one or a plurality of real-time data streams, one or a plurality of waveforms, as an aural output, or in any other suitable fashion.

Method 100 further comprises proceeding to input user modification (step 114), herein referred to as step 114, where step 114 comprises user 13 inputting commands relative to data displayed on interface 37. User 13 may, in one embodiment of the present invention, make changes in drug dosage delivery, make billing changes, lock-down sedation and analgesia system 22, alert a remote clinician of a potential problem, make data storage changes, input authorizations for drugs used with sedation and analgesia system 22, and/or other suitable inputs beneficial in ensuring patient 18 safety.

Following step 114, method 100 comprises proceeding to step 104, where data associated with user 13 input is transmitted to second transceiver 31. Method 100 may then proceed to step 103, where data is transmitted from second transceiver 31 to first transceiver 30. Method 100 may then proceed to step 102, where data is transmitted from first transceiver 30 to controller 14. In one embodiment of the present invention, input received by controller 14 from user 13 may be inputted into sedation and analgesia system 22, where method 100 will then return to step 101.

Figure 4:
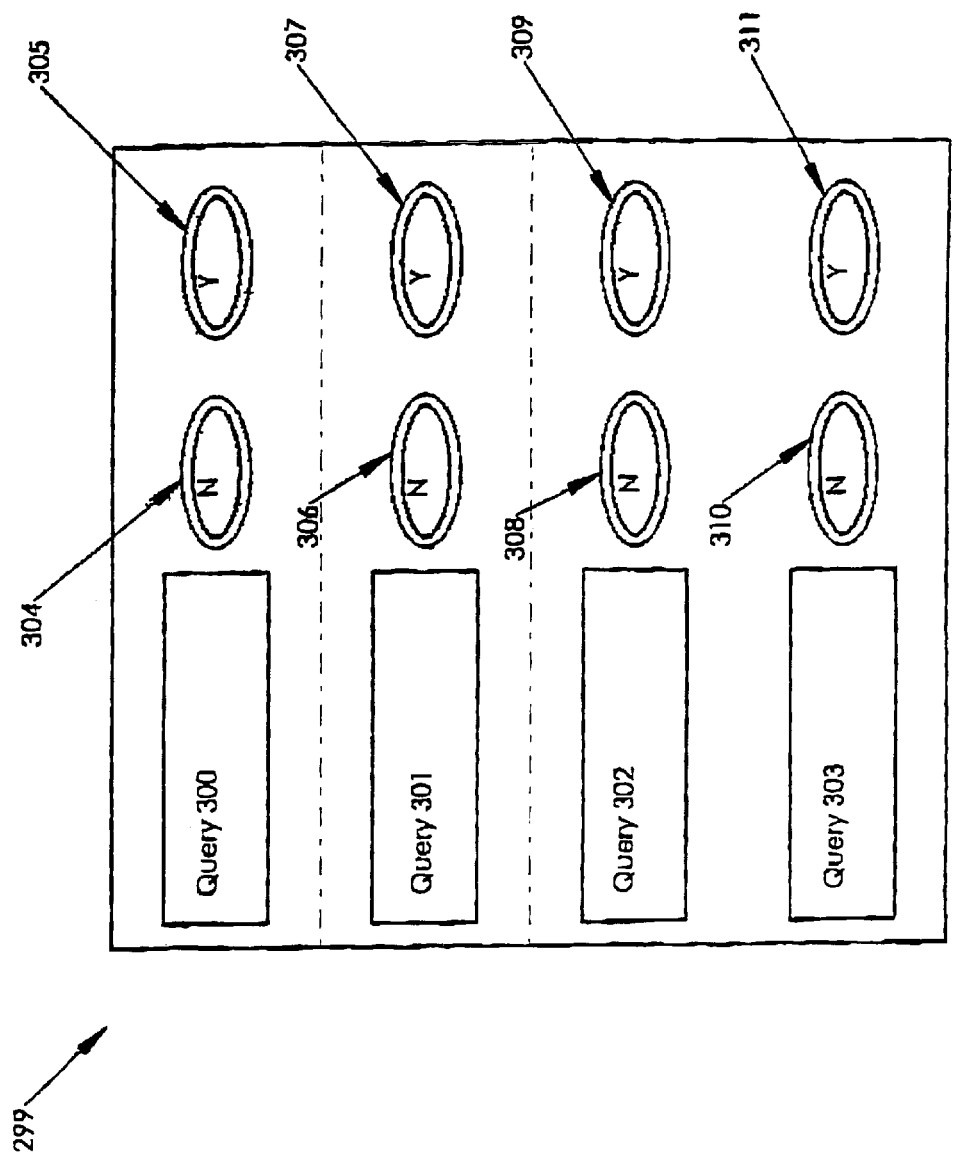
FIG. 4 illustrates one embodiment of a quality audit prompt in accordance with the present invention.

FIG. 4 illustrates one embodiment of quality audit prompt 299, where quality audit prompt 299 comprises query 300, query 301, query 302, query 303, no button 304, yes button 305, no button 306, yes button 307, no button 308, yes button 309, no button 310, and yes button 311. In one embodiment of the present invention buttons 304, 305 are associated with query 300, buttons 306, 307 are associated with query 301, buttons 308, 309 are associated with query 302, and buttons 310, 311 are associated with query 303. Quality audit prompt 299 is, in one embodiment of the present invention, integrated into user interface 12, where quality audit prompt 299 will be presented to user 13 upon completion of a medical procedure.

Query 300 comprises querying whether a fatality has occurred during a procedure, whether a severe complication has occurred during a procedure, or other suitable query related to an extremely negative patient episode. At the completion of a procedure, user 13 will be prompted by query 300 to press either no button 304 or yes button 305, where no button 304 indicates a no response to query 300 and yes button 305 indicates a yes response to query 300. For example, if query 300 asks user 13 whether a fatality occurred during the procedure, and a fatality did occur, user 13 will press yes button 305 to indicate and store the fatality. If a fatality did not occur, user 13 will press no button 304 indicating that no fatality occurred during the procedure. Quality audits are a common practice in hospitals and other organizations striving to comply with JCAHO and other regulatory agency requirements. These audits are often performed by nurses who are required to evaluate thousands of procedures from paper records that do not provide any consistent basis for evaluation. Often, performing a quality audit is a time consuming and tedious process, where gaining true insight into patterns related to mechanical or personnel failure are difficult at best. The present invention comprises providing quality audit prompt 299 at the completion of every procedure, where data related to patient 18 may be easily and efficiently stored and retrieved for quantitative evaluation.

Query 301 comprises querying, for example, whether a minor complication has occurred during a procedure, however other suitable queries related to regulatory compliance are consistent with the present invention. At the completion of a procedure, user 13 will be prompted by query 301 to press either no button 306 or yes button 307, where no button 306 indicates a no response to query 301 and yes button 307 indicates a yes response to query 301. For example, if query 301 asks user 13 whether a minor complication has occurred during the procedure, and a minor complication did occur, user 13 will press yes button 307 to indicate and store the minor complication event. If a minor complication did not occur, user 13 will press no button 306 indicating that no minor complications occurred during the procedure.

Query 302 comprises querying, for example, whether drug delivery associated with sedation and analgesia system 22 was inadequate, however other suitable queries related to regulatory compliance are consistent with the present invention. At the completion of a procedure, user 13 will be prompted by query 302 to press either no button 308 or yes button 309, where no button 308 indicates a no response to query 302 and yes button 309 indicates a yes response to query 302. For example, if query 302 asks user 13 whether drug delivery was inadequate, and drug delivery was inadequate, user 13 will press yes button 309 to indicate and store the occurrence of inadequate drug delivery. If there was no occurrence of inadequate drug delivery, user 13 will press no button 308 indicating that drug delivery was adequate.

Query 303 comprises querying, for example, whether user 13 feels the procedure should be evaluated in a quality audit, however other suitable queries related to regulatory compliance are consistent with the present invention. At the completion of a procedure, user 13 will be prompted by query 303 to press either no button 310 or yes button 311, where no button 310 indicates a no response to query 303 and yes button 311 indicates a yes response to query 303. For example, if query 303 asks user 13 whether the procedure should be evaluated in a quality audit, and user 13 believes there would be benefit in reviewing the events of the procedure, user 13 will press yes button 311 to indicate and store the request for review in a quality audit. If user 13 does not feel there is a need for the procedure to be reviewed in a quality audit, user 13 will press no button 310 indicating that no request has been made. It will be obvious to one of ordinary skill in the art that providing a plurality of queries related to providing regulatory compliance are consistent with the present invention.

The present invention comprises transmitting data from queries 300, 301, 302, 303 to server 33, data logging 34, and/or control 35, where data may be easily accessed and evaluated in a quality audit or related procedure intent on complying with regulatory standards. Data from queries 300, 301, 302, 303 may be transmitted to server 33, data logging 34, and/or control 35 in a manner consistent with method 100 illustrated in FIG. 3. Data from queries 300, 301, 302, 303 may also be stored internally in sedation and analgesia system 22, where data may be stored on a flash disk, super disk, or other suitable data storage device. Data may be transferred from the internal storage device of sedation and analgesia system 22 via a wireless connection, hardwired connections, or may be manually transferred from sedation and analgesia system 22 to any suitable interface 37. Data from queries 300, 301, 302, 303 may further be displayed on interface 37 in a manner consistent with method 100.

It is further contemplated that quality audit prompt 299 and transmission and display means associated with quality audit prompt 299 may be applied to a plurality of medical fields such as, for example, those fields involving patient monitoring, where a concise means of providing quantitative data related to patient condition is desirable. The present invention further comprises quality audit prompt 299 having queries related to medical system functionality, where user 13 may input whether a monitoring system or other medical system experienced any degree of complication.

The invention claimed is:

1. A sedation and analgesia system for providing sedation and/or pain relief without general anesthesia to patients undergoing a medical and/or surgical procedure, said system comprising:
   a plurality of patient health monitors adapted to be coupled to a plurality of patients undergoing a medical or surgical procedure, said patient health monitors generating a signal reflecting measurements of at least one monitored physiological condition of the patients;
   a controllable drug delivery device adapted to supply one or more sedative and/or analgesic drugs;
   at least one electronic controller having safe and/or effective parameters for said monitored physiological condition, said parameters indicating values for said measurements of said monitored physiological condition patient where said values correlate to safe and/or effective sedation during said procedure, and said electronic controller being adapted to receive said signal, compare said measurements reflected in said received signal with said parameters, and provide an alarm in the event said signal is outside of said safe and/or effective parameters; and
   a remote monitor and control system for receiving data from the sedation and analgesia system including said signal, and/or alarm and for displaying said signal in a display, pertaining to each patient and wherein an authorized user can modify, control and/or override the electronic controller through the remote monitor and control system.

2. The sedation and analgesia system according to claim 1, wherein the authorized user is an anesthetist and/or anesthesiologist.

3. The sedation and analgesia system according to claim 1, further comprising a remote memory device, wherein the remote monitor and control system and the remote memory device are interconnected such that the data received from the sedation and analgesia system is stored in the remote memory device.

4. The sedation and analgesia system according to claim 1, wherein the data received by the remote monitor and control system comprises one or more of the signals reflecting at least one physiological condition of the patient, a dose of drug supplied by the drug delivery controller, and information regarding maintenance performed on the sedation and analgesia system.

5. The sedation and analgesia system according to claim 1, wherein said display further comprises video transmissions of said procedure in addition to that of receiving sedation and/or analgesia being performed on said patient.

6. The sedation and analgesia system according to claim 1, wherein said remote monitor and control system receives data from a plurality sedation and analgesia systems.

7. A sedation and analgesia system for providing sedation and/or pain relief to a plurality of patients during a medical and/or surgical procedure, said system comprising:
   a patient health monitor adapted to be coupled to each patient to generate a signal reflecting at least one physiological condition of the patient;
   a drug delivery controller supplying one or more sedative and/or analgesic drugs to each patient;
   a device that stores safe parameters of at least one monitored patient physiological condition for each patient;
   a remote interface to the patient health monitors, the drug delivery controllers and the devices that stores the parameters, wherein said remote interface receives said signal and displays said signal with other patient data that is relevant to a safe physiological condition of each patient, and enables an authorized clinician to control or override said drug delivery controllers through said remote interface to insure that said sedative and/or analgesic drugs are supplied to said patients in a safe and effective manner.

8. The sedation and analgesia system according to claim 7, wherein the device that stores the parameters is remote from the patient health monitors and the drug delivery controllers.

9. The sedation and analgesia system according to claim 7, wherein the drug delivery controllers generates a signal reflecting the dose of drug delivered to a patient and wherein the parameters indicate one or more safe patient conditions, wherein the remote interface receives said signal reflecting the dose of drug delivered and in response modifies a supply rate of the drugs in accord with the parameters.

10. The sedation and analgesia system according to claim 9, wherein the remote interface displays drug delivery data simultaneously with video transmissions relevant to said separate procedure.

11. The sedation and analgesia system according to claim 7, further comprising a system state monitor for generating a signal reflecting a change in condition of the sedation and analgesia system, wherein the remote interface receives said signal reflecting said change in the sedation and analgesia system and in response manages the application of the drugs in accord with the change.

12. The sedation and analgesia system according to claim 11, wherein the remote interface locks down the sedation and analgesia system upon receipt of said signal reflecting said change in the sedation and analgesia system.

13. A method of operating a plurality of sedation and analgesia systems, said method comprising the steps of:
connecting to a first patient a first drug delivery device having a drug delivery controller supplying one or more sedation and/or analgesic drugs,
connecting to a second patient a second drug delivery device having a drug delivery controller supplying one or more sedation and/or analgesic drugs, said first and second drug delivery controllers each being coupled to an electronic controller which controls the delivery of the drugs to the patient;
attaching at least one patient health monitor device to each of said first and second patients, each health monitor device generating a value reflecting at least one physiological condition of a patient and being coupled to said electronic controller, said electronic controller having safe and/or effective parameters values for said monitored physiological condition,
remotely monitoring and displaying data reflecting drug dosage and other patient data reflecting each of said at least one said physiological conditions of the first and second patients and said safe and/or effective parameter values for said monitored physiological condition, and
enabling a remote authorized clinician of said system to view said data and to modify delivery of said drugs to each of said patients to achieve safe and effective drug delivery.

14. The method of operating a sedation and analgesia system according to claim 13, wherein the step of remotely monitoring data comprises remotely monitoring the value reflecting at least one physiological condition of a patient, a dose of drug supplied by the drug delivery device, and information regarding maintenance performed on the sedation and analgesia system.

15. The method of operating a sedation and analgesia system according to claim 14, wherein each of the electronic controllers also has parameters reflecting one or more of the dose of drug supplied by the drug delivery device, and information regarding maintenance performed on the sedation and analgesia system.

16. The method of operating a sedation and analgesia system according to claim 13, wherein data from the step of modifying the supply rate of the drugs to each of the first and second patients in accord with the parameters is displayed simultaneously with video transmissions relevant to the procedure in addition to that of receiving sedation and/or analgesia.

17. The method of operating a sedation and analgesia system according to claim 13, wherein the step of remotely monitoring data comprises remotely monitoring the dose of drug delivered to each of the patients and wherein the parameters indicate undesirable parameters for drug dosage, wherein each of the electronic controllers receives said signal reflecting the dose of drug delivered and in response manages the application of the drugs in accord with the parameters.

18. The method of operating a sedation and analgesia system according to claim 13, further comprising the step of updating billing information based on the data monitored remotely.

19. The method of operating a sedation and analgesia system according to claim 13, further comprising the step of presenting to the user a quality audit prompt through the user interface at the completion of a medical procedure.

20. A method of providing safe sedation without general anesthesia to one or more non-intubated patients during a medical and/or surgical procedure with a controllable drug delivery apparatus, said method comprising:
coupling said drug delivery apparatus to said one or more patients;
obtaining data reflecting one or more physiological conditions of said one or more patients and directing said data to an electronic controller, said electronic controller being adapted to control said drug delivery apparatus in accord with an algorithm;
providing a remote monitor and control apparatus to an authorized clinician for remotely observing said one or more physiological conditions of said one or more patients and for overriding said electronic controller in the event said one or more patients suffer abnormal conditions .

21. The method of providing safe sedation according to claim 20, wherein said drug is selected from a group comprising fentanil, remifentanil, propofol, and morphine.

* * * * *